US00RE37813E

(19) United States
(12) Reissued Patent
Cannata et al.

(10) Patent Number: US RE37,813 E
(45) Date of Reissued Patent: Aug. 6, 2002

(54) PROCESS FOR THE SYNTHESIS OF NABUMETONE

(75) Inventors: Vincenzo Cannata, Bologna; Amilcare Bertoni, Tarcento; Stefano Bianchi, Como, all of (IT)

(73) Assignee: Honeywell International Inc., Morristown, NJ (US)

(21) Appl. No.: 09/547,936

(22) Filed: Apr. 11, 2000

Related U.S. Patent Documents

Reissue of:
(64) Patent No.: 5,750,793
Issued: May 12, 1998
Appl. No.: 08/788,054
Filed: Jan. 23, 1997

(30) Foreign Application Priority Data

Feb. 21, 1996 (IT) ..... BO96A0078

(51) Int. Cl.[7] ..... C07C 45/65
(52) U.S. Cl. ..... 568/315; 568/314; 568/324
(58) Field of Search ..... 568/314, 315, 568/324

(56) References Cited

U.S. PATENT DOCUMENTS

| | | | | |
|---|---|---|---|---|
| 2,544,562 | A | 3/1951 | Michael | 260/331 |
| 4,061,779 | A | 12/1977 | Lake et al. | 424/331 |
| 4,221,741 | A | 9/1980 | Gaster | 568/314 |
| 5,344,992 | A | 9/1994 | Drewes et al. | 568/314 |
| 5,545,762 | A | 8/1996 | Murh | 568/346 |

FOREIGN PATENT DOCUMENTS

| | | |
|---|---|---|
| NL | 9700353 | 9/1987 |

OTHER PUBLICATIONS

Chemical Abstract of Netherlands Patent 8700353.
Chemical Abstract of Netherlands Patent 8700354.
Chemical Abstract of Netherlands Patent 8700356.
Chemical Abstract of Netherlands Patent 8700357.
Chemical Abstract of Netherlands Patent 8700358.
Beecham Group, Chemical Abstracts of Dutch patent 8700, 353, vol. 108, No. 204.339a, 1987.

*Primary Examiner*—James H. Reamer
(74) *Attorney, Agent, or Firm*—Colleen Szuch

(57) ABSTRACT

New process for the synthesis of the antiinflammatory drug known as nabumetone that consists in reacting 2-acetyl-5-bromo-6-methoxynaphthalene with an alkyl acetate in presence of an alkaline alcoholate to get 4-(5-bromo-6-methoxy-2-naphthyl)-4-hydroxybut-3-en-2-one that by catalytic hydrogenation in a polar solvent and in presence of a base gives 4-(6-methoxy-2-naphthyl)butan-2-one known as nabumetone.

40 Claims, No Drawings

PROCESS FOR THE SYNTHESIS OF NABUMETONE

Matter enclosed in heavy brackets [ ] appears in the original patent but forms no part of this reissue specification; matter printed in italics indicates the additions made by reissue.

BACKGROUND OF PRIOR ART

Nabumetone, 4-(6-methoxy-2-naphthyl)butan-2-one, is a known antiinflammatory drug. It has been synthesized and claimed at first in U.S. Pat. No. 4,061,779 granted on 1977. Other processes for the synthesis of nabumetone have subsequently been described and claimed. The synthesis of nabumetone by catalytic hydrogenation of 4-(6-methoxy-2-naphthyl)-4-hydroxybut-3-en-2-one obtained by condensation of 2-acetyl-6-methoxynaphthalene with ethyl acetate in presence of sodium hydride is described in U.S. Pat. No. 4,221,741 granted on 1980. The condensation reaction was carried out in anhydrous dimethylsulfoxide and under nitrogen. This condensation reaction, notwithstanding good yields, shows severe drawbacks, when used at industrial level, in terms of costs and of safety because of the use of remarkable amounts of sodium hydride and the consequent necessity of working in perfectly anhydrous and de-aerated ambient in order to avoid any risk of explosions.

The catalytic hydrogenation of compounds of formula

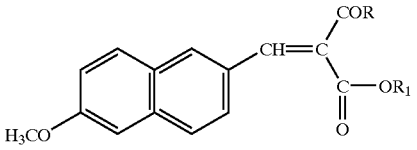

wherein R and $R_1$ are alkyl or alkylaryl groups, compounds obtained by condensation of 6-methoxy-2-naphthaldehyde with alkyl or alkylaryl acetoacetates, is described in U.S. Pat. Nos. 4,247,709 and 4,270,004 granted on 1981. Also this process is not advantageous from an economical point of view because of the high industrial cost of the 6-methoxy-2-naphthaldehyde. A great number of patent applications on alternative methods of synthesis of nabumetone and, among these, the published Dutch patent application NL 8700353, has subsequently been filed. In this patent application a process is described wherein 2-acetyl-5-bromo-6-methoxynaphthalene of formula

II

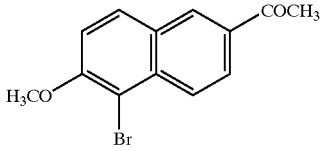

is reacted with ethyl acetate in presence of an oily 80% dispersion of sodium hydride to give the sodium salt of the 4-(5-bromo-6-methoxy-2-naphthyl)-4-hydroxybut-3-en-2-one of formula

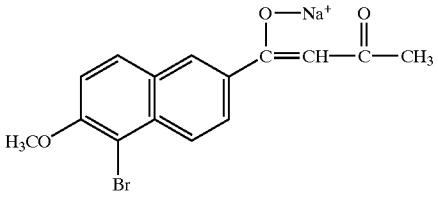

that is reduced to 4-(6-methoxy-2-naphthyl)butan-2-one by means of a catalytic hydrogenation by using 10% palladium on carbon as catalyst in presence of an excess of sulfuric acid with respect to the amount necessary to free the 4-(5-bromo-6-methoxy-2-naphthyl)-4-hydroxybut-3-en-2-one, or its tautomer, from its sodium salt. Moreover, during the hydrogenation reaction hydrobromic acid forms which, if not neutralized, makes even more acidic the reaction ambient causing the formation of high amounts of reaction's by-products and requiring costly acid-proof equipments. The poor selectivity of the reaction is made clear by the fact that the raw material coming from the hydrogenation has to be purified many times in order to obtain the necessary quality and the final yield is only 57%.

SUMMARY OF THE INVENTION

Present invention is a decisive improvement of the process described in the published Dutch patent application NL 8700353 for both reactions, the condensation and the hydrogenation reaction, used to get the nabumetone starting from the 2-acetyl-5-bromo-6-methoxynaphthalene intermediate. The condensation reaction described in the present invention is carried out in presence of an alkaline alcoholate, much less costly and more safe than sodium hydride used in NL 8700353. The reaction of hydrogenation is carried out, in the present inventon, not only in absence of sulfuric acid but even in presence of a basic substance in such an amount that most of the hydrobromic acid that comes from the hydrogenation reaction is neutralized so freeing from the reaction ambient the most of a reagent that, when present in remarkable amounts, is able to produce side-products which contaminate the desired product, make necessary a double purification and, finally, lower the end yield.

The hydrogenation reaction according to the invention described later can be carried out in standard equipments, gives a cleaner raw product from the reaction, which needs only one purification step, through crystallization or bisulphite complex, allowing the achievement of higher yields.

Summing up, the process described in NL 8700353 is a scarcely convenient process for the industrial manufacture of nabumetone, because of the high cost and unsafety of the reagent, the low yield and the need to make it in costly particular equipments. The process described in the present invention, constitues a remarkable improvement in the industrial manufacture of nabumetone also with reference to the already mentioned U.S. Pat. No. 4,221,741 because it uses the cheaper 4-(5-bromo-6-methoxy-2-naphthyl)-4-hydroxybut-3-en-2-one, or its tautomer, obtained from 2-acetyl-5-bromo-6-methoxynaphthalene that is an intermediate in the synthesis of the 2-acetyl-6-methoxynaphthalene described in our European patent EP 0440930 from which the 4-(-6-methoxy-2-naphthyl)-4-hydroxybut-3-en-2-one, or its tautomer, used in the abovementioned U.S. Pat. No. 4,221,741, is obtained. In fact, the reaction of acylation of 2-methoxynaphthalene carried out under normal conditions gives 1-acetyl-2-methoxynaphthalene instead of 2-acetyl-6-methoxynaphthalene. The reaction to get 2-acetyl-6-methoxynaphthalene has to be carried out in specified solvents very toxic and dangerous to handle like nitrobenzene, with which low yields are obtained, or liquid hydrofluoric acid or, as in the case of our European patent EP 0440930, position 1 has to be first protected by making 1 -bromo-2-methoxynaphthalene that by acylation under normal conditions gives 2-acetyl-5-bromo-6-methoxynaphthalene with yields higher than 90% from which, by dehalogenation, 2-acetyl-6-methoxynaphthalene is obtained.

DESCRIPTION OF THE INVENTION

Object of the present invention is a new process for the synthesis of the 4-(6-methoxy-2-naphthyl)butan-2-one of formula I

I

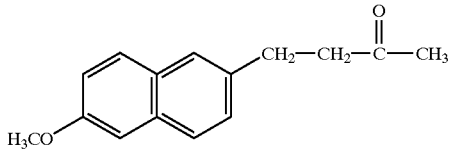

antiinflammatory drug known under the name of nabumetone. The synthesis process goes through two steps shown in the following scheme:

Scheme 1

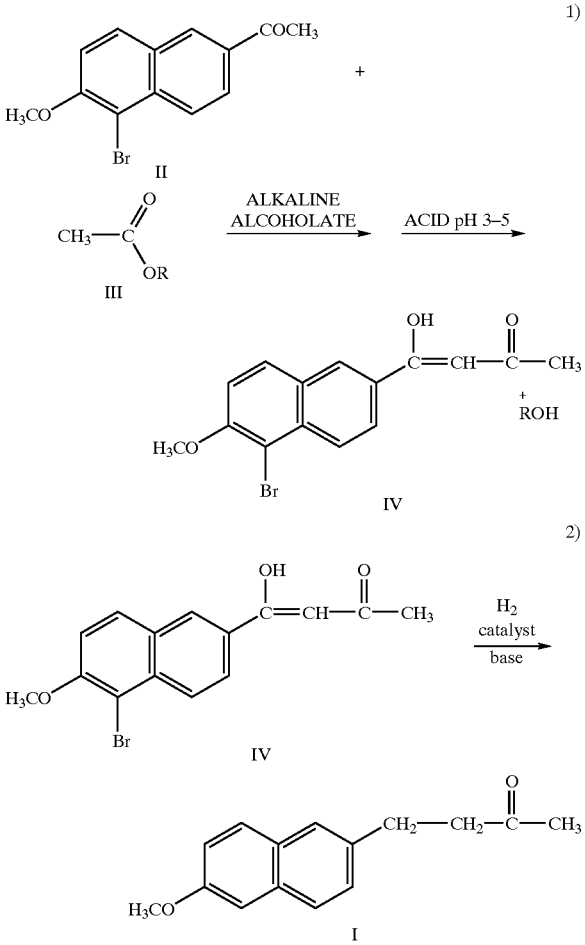

A molar equivalent of 2-acetyl-5-bromo-6-methoxynaphthalene of formula II is reacted with an alkyl acetate of formula III, wherein R represents an alkyl group containing from 1 to 6 carbon atoms, in presence of from 1 to 3 molar equivalents of an alkaline alcoholate to get the 4-(5-bromo-6-methoxy-2-naphthyl)-4-hydroxybut-3-en-2-one of formula IV. The reaction mixture is reacted for a period of time from 0.5 to 6 hours at a temperature from 10° C. to 90° C. The same alkyl acetate used as reagent, preferably ethyl acetate, n-butyl acetate, n-propyl acetate or isopropyl acetate, is also used as reaction solvent, alone or in mixture with other solvents like toluene, acetonitrile or N,N-dimethylformamide. A sodium or potassium alcoholate of an alcohol containing from 1 to 4 carbon atoms is preferably used as alkaline alcoholate. The product of formula IV is then recovered from the ambient of reaction by acidifying at a pH value from 3 to 5 with an aqueous solution of an organic or inorganic acid, by optionally warming the reaction mixture for 15–30 minutes at the boiling temperature in order to improve the filterability and by subsequently cooling at temperatures from 10° C. to 0° C. The product of formula IV is obtained with high yields, comprised between 85% and 95% with respect of the starting product of formula II, after filtration, washings of the solid with water and with the reaction solvent and drying in oven under vacuum. The 4-(5-bromo-6-methoxy-2-naphthyl)-4-hydroxybut-3-en-2-one of formula IV so obtained is submitted to catalytic hydrogenation with hydrogen in presence of a base to give the desired 4-(6-methoxy-2-naphthyl)butan-2-one of formula I, antiinflammatory drug known as nabumetone. The reaction of hydrogenation takes place in a hydrogenator where a molar equivalent of the compound of formula IV is hydrogenated with hydrogen at a pressure from 1 to 10 atmospheres for a period of time from 2 to 24 hours, preferably from 4 to 12 hours, and at a temperature from room temperature to 90° C., preferably from 30° C. to 60° C., in presence of an amount of base comprised from 0.30 to 0.99 molar equivalents, preferably from 0.90 to 0.98 molar equivalents, of an amount of a catalyst of hydrogenation from 0.005 to 0.05 molar equivalents and of a polar solvent or of its mixtures with polar or non-polar solvents. Straight or branched alcohols, cyclic or straight ethers, aliphatic amides or nitrites can be usefully used as polar solvents, while straight or branched aliphatic hydrocarbons, aromatic hydrocarbons or halogenated aliphatic hydrocarbons can be usefully used as non-polar solvents.

The bases preferred in the realization of the present invention are acetates, carbonates and bicarbonates of the alkali metals and the aromatic or tertiary aliphatic amines; acetates and carbonates of sodium or potassium are particularly preferred in carrying out the invention. Palladium on carbon at 5% or 10% concentration is the hydrogenation catalyst preferred in carrying out the invention. Alcohols containing from 1 to 6 carbon atoms and their mixtures with water or non-polar solvents are the solvents preferred in the realization of the invention. At the end of the reaction of hydrogenation, after having eliminated the catalyst by filtration, the reaction mixture is concentrated under vacuum. The obtained oily substance is purified either by crystallization from polar solvents, preferably alcohols containing from 1 to 6 carbon atoms, or by forming the bisulphite complex with sodium bisulphite in polar solvents, like N,N-dimethylformamide, alcohols containing from 1 to 6 carbon atoms ethers or mixtures thereof with water. The crystalline bisulphite complex which forms is isolated by filtration and restores the product of formula I by treatment with an aqueous solution of hydroxide, carbonate or bicarbonate of an alkali metal. The overall yields of the hydrogenation and of the subsequent purification are between 70% and 80% with respect to the compound of formula IV.

The examples of hydrogenation 3 and 4 wherein lower amounts of base are used, respectively 0.33 and 0.67 molar equivalents, with respect to the preferred amounts of base, comprised from 0.90 to 0.98 molar equivalents, show a significant decrease of the yields of hydrogenation, respectively 52.8% and 66%. This experimental result is an evident demonstration of the inventive level of the process described in the present invention.

The examples reported underneath have to be considered as a further illustration of the invention and not as an its limitation.

EXAMPLE 1

4-(5-Bromo-6-methoxy-2-naphthyl)-4-hydroxybut-3-en-2-one 139.4 Grams (0.499 moles) of 2-acetyl-5-bromo-6-methoxynaphthalene and 1450 ml of ethyl acetate are placed in a flask equipped with refrigerator and stirrer and, under stirring and at the temperature of 45° C., 30 g (0.556 moles) of sodium methoxide are added. The temperature of the reaction mixture goes up to 55° C. and is kept at 65° C. for one hour, then other 10 g (0.185 moles) of sodium methoxide are added and, after half an hour, still other 10 g (0.185 moles) of sodium methoxide, always under stirring and keeping the temperature at 65° C. for another hour and half. The reaction mixture is then cooled to room temperature and brought to pH 4 by adding a concentrated aqueous solution of hydrochloric acid. The reaction mixture is then heated to reflux for 15 minutes, cooled to 5° C. in one hour and kept at this temperature for 2 hours. The precipitated solid is filtered, abundantly washed with water on the filter, then washed with ethyl acetate and dried in oven under vacuum obtaining 145.7 g of product with a yield equal to 90.8%.

EXAMPLE 2

4-(5-Bromo-6-methoxy-2-naphthyl)-4-hydroxybut-3-en-2-one

50 Grams (0.179 moles) of 2-acetyl-5-bromo-6-methoxynaphthalene and 200 ml of n-butyl acetate are placed in a flask equipped with refrigerator and stirrer and, under stirring and at the temperature of 15° C., 14.5 g (0.268 moles) of sodium methoxide are added. The temperature of the reaction mixture goes up to 25° C. and is kept at this value for 30 minutes, then the mixture is warmed at 65° C. for one hour, is added with 100 ml of water and is brought to pH 4 by adding a concentrated aqueous solution of hydrochloric acid. The reaction mixture is then cooled to 0°÷5° C. and kept at this temperature for one hour. The solid is filtered, abundantly washed with water on the filter, then washed with butyl acetate and dried in oven under vacuum obtaining 53 g of product with a yield equal to 92%.

EXAMPLE 3

4-(6-Methoxy-2-naphthyl)butan-2-one

48 Grams (0.150 moles) of 4-(5-bromo-6-methoxy-2-naphthyl)-4-hydroxybut-3-en-2-one, 6.1 g of sodium acetate hydrate containing 32.4% of water, equivalent to 0.050 moles of sodium acetate, 4 g of a 50% suspension in water of 10% palladium on carbon, equivalent to 0.0019 moles of palladium, and 500 ml of methanol are put in a hydrogenator. The hydrogenator is washed with nitrogen in order to eliminate the oxygen and then hydrogen is introduced at the pressure of 2 atmospheres. The temperature of reaction is kept at 40° C. for a period of time of 6 hours, then the hydrogen is let off, the hydrogenator is washed with nitrogen and the reaction mixture is filtered to eliminate the catalyst. The solution is brought to pH 6 with a 5% aqueous solution of sodium hydroxide and concentrated under vacuum. The oily residue is dissolved into 130 ml of isopropanol and 30 ml of N,N-dimethylformamide and the solution is added with 45 ml of water and 17.6 g of sodium bisulfite obtaining a suspension that is stirred for one hour at 60° C., then is cooled to 5° C. and is filtered. The obtained solid is washed with 75 ml of methanol, suspended in 200 ml of a 5% aqueous solution of sodium hydroxide and kept under stirring at room temperature for three hours. The suspension is then filtered, the solid is washed with water until neutrality and dried in oven under vacuum obtaining 18 g of product with a yield equal to 52.8%.

EXAMPLE 4

4-(6-Methoxy-2-naphthy)butan-2-one

The reaction described in example 3 is repeated with the sole changes of doubling the amount of sodium acetate hydrate containing 32.4% of water, 12.22 g equivalent to 0.100 moles of sodium acetate, and of lowering the hydrogenation time to five hours. In this way 22.5 g of product are obtained with a yield equal to 66%.

EXAMPLE 5

4-(6-Methoxy-2-naphthyl)butan-2-one

The reaction described in example 3 is repeated with the sole changes of nearly triplicating the amount of sodium acetate hydrate containing 32.4% of water, 17.60 g equivalent to 0.145 moles of sodium acetate, and of lowering the hydrogenation time to five hours. The oil obtained, as in example 3, by evaporating the solvent at the end of the reaction is treated with 300 ml of toluene and 100 ml of water and after 15 minutes of stirring the two layers are separated. The aqueous phase is discarded while the organic phase is evaporated under vacuum at 70° C. obtaining an oil that is dissolved into 100 ml of methanol. The solution is kept at 0° C. for two hours and the precipitated solid is filtered, washed with 15 ml of methanol cooled to 0° C. and dried in oven under vacuum. In this way 21.7 g of product are obtained. The methanolic filtrates from crystallization and washing are concentrated under vacuum to half volume so obtaining, after cooling to 0° C., the crystallization of other 4 g of product with an overall yield equal to 75.3%.

EXAMPLE 6

4-(6-Methoxy-2-naphthyl)butan-2-one 24.72 Grams (0.077 moles) of 4-(5-bromo-6-methoxy-2-naphthyl)-4-hydroxybut-3-en-2-one, 4.57 g of anhydrous sodium acetate and 2.58 g of sodium acetate trihydrate, equivalent to 0.075 moles of sodium acetate, 2 g of a 50% suspension in water of 5% palladium on carbon, equivalent to 0.00047 moles of palladium, and 200 ml of methanol are put in a hydrogenator. The hydrogenator is washed with nitrogen in order to eliminate the oxygen and then hydrogen is introduced at the pressure of three atmospheres. The reaction temperature is kept at 40° C. for a period of time of 6 hours, then the hydrogen is let off, the hydrogenator is washed with nitrogen and the reaction mixture is filtered in order to eliminate the catalyst. The solution is brought to pH 6 with a 5% aqueous solution of sodium hydroxide and concentrated under vacuum. The oily residue is treated with 150 ml of toluene and 50 ml of water and after stirring for 15 minutes the two layers are separated. The aqueous phase is discarded while the organic phase is evaporated under vacuum at 70° C. obtaining an oil that is dissolved in 50 ml of methanol. The solution is kept for 2 hours at 0° C. and the precipitated solid is filtered, washed with 10 ml of methanol cooled to 0° C. and dried in oven under vacuum. The methanolic filtrates from crystallization and washing are concentrated under vacuum at half volume so obtaining, after cooling to 0° C., the crystallization of other product that is dried in oven under vacuum. 14 Grams of product are obtained in totality with an overall yield equal to 79.7%.

EXAMPLE 7

4-(6-Methoxy-2-naphthyl)butan-2-one

The reaction described in example 6 is repeated with the changes of using potassium carbonate instead of sodium acetate and of doubling the reaction time until 12 hours. 5.15 Grams of potassium carbonate equivalent to 0.037 moles have been used and 13.7 g of product are obtained with a yield equal to 78%.

EXAMPLE 8

4-(6-Methoxy-2-naphthyl)butan-2-one 49.44 Grams (0.154 moles) of 4-(5-bromo-6-methoxy-2-naphthyl)-4-hydroxybut-3-en-2-one, 12.24 g (0.149 moles) of anhydrous sodium acetate, 4 g of a 50% suspension in water of 5% palladium on carbon, equivalent to 0.00094 moles of palladium and 400 ml of isopropanol are put into a hydrogenator. The hydrogenator is washed with nitrogen in order to eliminate the oxygen and then hydrogen is introduced at the pressure of 2.5 atmospheres. For a period of time of 9 hours the temperature of reaction is kept at 50° C., then the hydrogen is let off, the hydrogenator is washed with nitrogen and the reaction mixture is filtered in order to eliminate the catalyst. The solution is concentrated to 130 ml, diluted with 45 ml of water, heated to 60° C. and added with 18.2 g of sodium metabisulfite. The reaction mixture is kept for one hour at 60° C. and then is cooled to 0° C. The so obtained suspension is kept at 0° C. for two hours and then is filtered; the solid is washed with 60 ml of isopropanol cooled to 0° C. and then is suspended in a mixture made by 70 ml of a 10% aqueous solution of sodium hydroxide and 270 ml of toluene. The reaction mixture is stirred for one hour and half at room temperature, then is heated at 60° C. and the layers are separated. The organic phase is washed with 60 ml of water and is concentrated under vacuum at 60° C. until an oil is obtained which solidifies by cooling. The solid is dissolved at 60° C. in 40 ml of isopropanol and the resulting solution is cooled to 0° C. in two hours. The obtained suspension is kept for one hour at this temperature, filtered, washed with 10 ml of cold isopropanol and dried in oven under vacuum until constant weight. 26.3 Grams of nabumetone are obtained with a yield equal to 74.8%.

EXAMPLE 9

4-(6-Methoxy-2-naphthyl)butan-2-one 24.72 Grams (0.077 moles) of 4-(5-bromo-6-methoxy-2-naphthyl)-4-hydroxybut-3-en-2-one, 6 g (0.073 moles) of anhydrous sodium acetate, 2 g of a 50% suspension in water of 5% palladium on carbon, equivalent to 0.00047 moles of palladium, 180 ml of isopropanol and 20 ml of toluene are put into a hydrogenator. The hydrogenator is washed with nitrogen in order to eliminate the oxygen and then hydrogen is introduced at the pressure of one atmosphere. The temperature of reaction is kept at 60° C. for a period of time of 9 hours, then the hydrogen is let off, the hydrogenator is washed with nitrogen and the reaction mixture is filtered in order to eliminate the catalyst. The solution is brought to pH 6 with a 5% aqueous solution of sodium hydroxide and concentrated under vacuum. The oily residue is treated with 150 ml of toluene and 50 ml of water and after stirring for 15 minutes the two layers are separated. The aqueous phase is discarded while the organic phase is evaporated under vacuum at 70° C. obtaining an oil that is dissolved in 70 ml of isopropanol; the solution is diluted with 25 ml of water, heated at 60° C. and added with 9.1 g of sodium metabisulfite. The reaction mixture is kept for one hour at 60° C. and then cooled to 0° C. The resulting suspension is kept for 2 hours at 0° C. and filtered and the solid is washed with 30 ml of isopropanol cooled to 0° C. The so obtained solid is then suspended in a mixture made by 35 ml of a 10% aqueous solution of sodium hydroxide and by 135 ml of toluene.

The mixture is stirred for one hour and half at room temperature and then is heated at 60° C. The layers are separated and the organic phase is washed with 30 ml of water and concentrated under vacuum at 60° C. until an oil is obtained which solidifies by cooling. The solid is dissolved in 20 ml of isopropanol at 60° C. and the resulting solution is cooled to 0° C. in 2 hours. The obtained suspension is kept at this temperature for one hour, filtered, washed with 5 ml of cold isopropanol and dried in oven under vacuum until constant weight. 13.8 Grams of nabumetone are obtained with a yield equal to 78.5%.

We claim:

1. A process for the synthesis of 4-(6-methoxy-2-naphthyl)butan-2-one of formula I

I

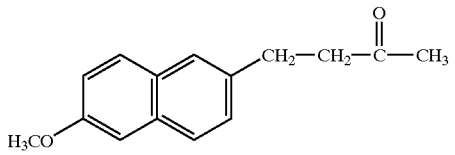

which comprises the steps of: a) reacting a molar equivalent of 2-acetyl-5-bromo-6-methoxynaphthalene of formula II

II

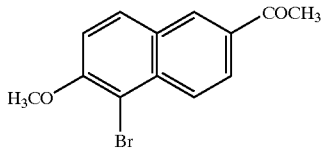

with an alkyl acetate of formula III

III

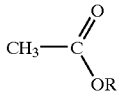

wherein R is an alkyl group containing from 1 to 6 carbon atoms, in a solvent, said solvent being a member selected from the group consisting of said alkyl acetate of formula III and mixtures of said alkyl acetate of formula III with toluene, acetonitrile or N,N-demethylformamide in presence of 1–3 molar equivalents of an alkaline alcoholate for a period of time from 0.5 to 6 hours at a temperature of 10° C.–90° C. whereby 4-(5-bromo-6-methoxy-2-naphthyl)-4-hydroxybut-3-en-2-one of formula IV is obtained

IV

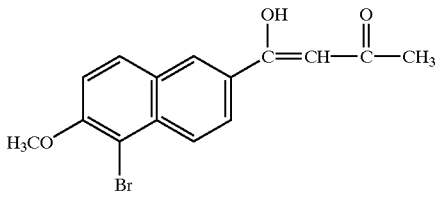

after acidifying the reaction mixture at a pH value of 3–5 by means of an aqueous solution of an organic or inorganic acid; b) submitting to catalytic hydrogenation a molar equivalent of said compound of formula IV with hydrogen at a pressure of 1–10 atmospheres, for a period of time of 2–24 hours, at a temperature from room temperature to 90° C., in presence of from 0.005 to 0.05 molar equivalents of a hydrogenation catalyst and 0.30 to 0.99 molar equivalents of a base; c) filtering the mixture from step b) and concentrating it under vacuum whereby an oily product is formed; d) purifying said oily product from step c) to obtain the pure compound of formula I.

2. The process according to claim 1 wherein step d) is carried out by crystallization from an alcohol containing from 1 to 6 carbon atoms.

3. The process according to claim 1 wherein step d) is carried out through formation of the crystalline bisulfite complex by reaction with sodium bisulfite in a polar solvent or a mixture of said polar solvent with water and treatment of said resulting bisulfite complex with an aqueous solution of hydroxide, carbonate or bicarbonate of an alkali metal in order to recover the 4-(6-methoxy-2-naphthyl)butan-2-one of formula I.

4. The process according to claim 1 wherein in step a) said alkaline alcoholate is a sodium or potassium alcoholate of an alcohol containing from 1 to 4 carbon atoms.

5. The process according to claim 1 wherein said hydrogenation catalyst in step b) is 5% or 10% palladium on carbon.

6. The process according to claim 1 wherein in step b) the amount of said base is from 0.66 to 0.98 molar equivalents, and said base is an acetate or a carbonate of sodium or potassium.

7. The process according to claim 1 wherein step b) is carried out in a solvent which is an alcohol containing from 1 to 6 carbon atoms or mixtures thereof with water or non-polar solvents.

*8. A process for the synthesis of 4-(6-methoxy-2-naphthyl) butan-2-one of formula I*

*I*

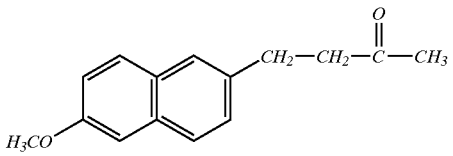

*which comprises:*

*a) reacting 2-acetyl-5-bromo-6-methoxynaphthalene of formula II*

*II*

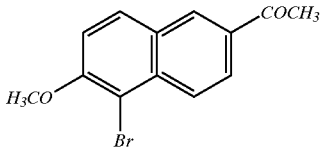

*with an alkyl acetate of formula III*

*III*

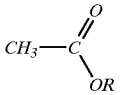

*wherein R represents an alkyl group containing from 1 to 6 carbon atoms, in the presence of an alkaline alcoholate to form 4-(5-bromo-6-methoxy-2-naphthyl)-4-hydroxybut-3-en-2-one of formula IV*

*IV*

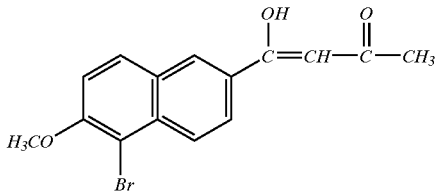

*b) reacting the compound of formula IV with hydrogen, in the presence of a hydrogenation catalyst and a base; and*

*c) optionally recovering the product.*

*9. The process of claim 8 wherein the compound of formula IV is acidified prior to catalytic hydrogenation.*

*10. The process of claim 8 wherein the compound of formula IV is acidified at a pH of from 3 to 5 prior to catalytic hydrogenation.*

*11. The process of claim 8 wherein one molar equivalent of the 2-acetyl-5-bromo-6-methoxynaphthalene is reacted with the alkyl acetate.*

*12. The process of claim 8 wherein the 2-acetyl-5-bromo-6-methoxynaphthalene is reacted with the alkyl acetate in a solvent.*

*13. The process of claim 8 wherein the 2-acetyl-5-bromo-6-methoxynaphthalene is reacted with the alkyl acetate in a solvent selected from the group consisting of the alkyl acetate of formula III, and mixtures of the alkyl acetate of formula III with toluene, acetonitrile or N,N-dimethylformamide.*

*14. The process of claim 8 wherein the 2-acetyl-5-bromo-6-methoxynaphthalene is reacted with the alkyl acetate in the presence of 1–3 molar equivalents of the alkaline alcoholate.*

*15. The process of claim 8 wherein the 2-acetyl-5-bromo-6-methoxynaphthalene is reacted with the alkyl acetate for from about 0.5 to about 6 hours.*

*16. The process of claim 8 wherein the 2-acetyl-5-bromo-6-methoxynaphthalene is reacted with the alkyl acetate at a temperature of from about 10° C. to about 90° C.*

*17. The process of claim 8 wherein the 2-acetyl-5-bromo-6-methoxynaphthalene is reacted with the alkyl acetate and then the result acidified with an aqueous solution of an organic or inorganic acid.*

*18. The process of claim 8 wherein in step a) said alkaline alcoholate is a sodium or potassium alcoholate of an alcohol containing from 1 to 4 carbon atoms.*

19. The process of claim 8 wherein step a) is conducted in a solvent selected from the group consisting of the alkyl acetate of formula III, and mixtures of the alkyl acetate of formula III with toluene, acetonitrile or N,N-dimethylformamide; in the presence of 1–3 molar equivalents of an alkaline alcoholate which is a sodium or potassium alcoholate of an alcohol containing from 1 to 4 carbon atoms; for from about 0.5 to about 6 hours and at a temperature of from about 10° C. to about 90° C., then acidifying the compound of formula IV with an aqueous solution of an organic or inorganic acid at a pH of from 3 to 5.

20. The process of claim 8 wherein one molar equivalent of the compound of formula IV is reacted with hydrogen in the presence of 0.005 to 0.05 molar equivalent of a hydrogenation catalyst and 0.30 to 0.99 molar equivalent of a base.

21. The process of claim 8 wherein the hydrogenation is conducted at a pressure of from 1–10 atmospheres.

22. The process of claim 8 wherein the hydrogenation is conducted at a temperature of from room temperature to 90° C.

23. The process of claim 8 wherein the hydrogenation is conducted for a period of time of 2–24 hours.

24. The process of claim 8 wherein said hydrogenation catalyst in step b) comprises5% or 10% palladium on carbon.

25. The process of claim 8 wherein step b) the base is selected from the group consisting of an acetate or a carbonate of sodium or potassium and is present in an amount of from 0.30 to 0.99 molar equivalents.

26. The process of claim 8 wherein step b) is conducted in a solvent comprising an alcohol having from 1 to 6 carbon atoms, mixtures of an alcohol having from 1 to 6 carbon atoms with water, or non-polar solvents.

27. The process according to claim 8 wherein the alkaline alcoholate is selected from the group consisting of sodium and potassium alcoholates of alcohols containing from 1 to 4 carbon atoms, the catalyst of hydrogenation comprises 5% or 10% palladium on carbon, the amount of base is from 0.90 to 0.98 molar equivalents, the base is selected from acetates and carbonates of sodium or potassium and the hydrogenation is conducted in the presence of a solvent selected from the group consisting of alcohols containing from 1 to 6 carbon atoms and mixtures thereof with water or non-polar solvents.

28. The process of claim 8 wherein step b) is conducted by reacting one molar equivalent of the compound of formula IV with hydrogen, in the presence of 0.005 to 0.05 molar equivalent of a 5% or 10% palladium on carbon hydrogenation catalyst and 0.30 to 0.99 molar equivalent of a base selected from the group consisting of an acetate or a carbonate of sodium or potassium; in a solvent comprising one or more components selected from the group consisting of an alcohol having from 1 to 6 carbon atoms, mixtures of an alcohol having from 1 to 6 carbon atoms with water, or non-polar solvents; at a pressure of from 1–10 atmospheres, a temperature of from room temperature to 90° C. and for a period of time of 2–24 hours.

29. The process of claim 8 wherein the product 4-(6-methoxy-2-naphthyl)butan-2-one of formula I is recovered.

30. The process of claim 8 further comprising filtering the product of step b) to recover the compound of formula I and concentrating the compound of formula I under vacuum.

31. The process of claim 30 further comprising purifying the compound of formula I.

32. The process of claim 30 further comprising purifying the compound of formula I by crystallizing the compound of formula I from an alcohol containing from 1 to 6 carbon atoms.

33. The process of claim 30 further comprising purifying the compound of formula I by forming a crystalline bisulfite complex by reacting the product of step b) with sodium bisulfite in a polar solvent or a mixture of a polar solvent with water, and treating the resulting bisulfite complex with an aqueous solution of a hydroxide, carbonate or bicarbonate of an alkali metal to thereby recover the purified 4-(6-methoxy--2-naphthyl)butan-2-one of formula I.

34. The process of claim 8 wherein step c) is conducted by filtering the product of step b) to recover the compound of formula I and concentrating the compound of formula I under vacuum; and purifying the compound of formula I either by crystallizing the compound of formula I from an alcohol containing from 1 to 6 carbon atoms, or forming a crystalline bisulfite complex by reacting the product of step b) with sodium bisulfite in a polar solvent or a mixture of a polar solvent with water, and treating the resulting bisulfite complex with an aqueous solution of a hydroxide, carbonate or bicarbonate of an alkali metal to thereby recover the purified 4-(6-methoxy-2-naphthyl)butan-2-one of formula I.

35. The process of claim 34 wherein the purifying is conducted by crystallizing the compound of formula I from an alcohol containing from 1 to 6 carbon atoms.

36. The process of claim 34 wherein the purifying is conducted by forming a crystalline bisulfite complex by reacting the result of step b) with sodium bisulfite in a polar solvent or a mixture of a polar solvent with water, and treating the resulting bisulfite complex with an aqueous solution of a hydroxide, carbonate or bicarbonate of an alkali metal to thereby recover the 4-(6-methoxy-2-naphthyl) butan-2-one of formula I.

37. A process for the synthesis of 4-(6-methoxy-2-naphthyl)butan-2-one of formula I

I

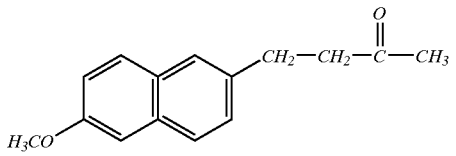

which comprises:

a) reacting a molar equivalent of 2-acetyl-5-bromo-6-methoxyraphthalene of formula II

II

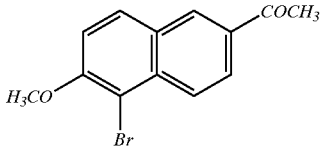

with an alkyl acetate of formula III

III

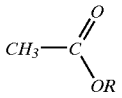

wherein R represents an alkyl group containing from 1 to 6 carbon atoms, in presence of from 1 to 3 molar equivalents of an alkaline alcoholate for a period of time from 0.5 to 6 hours at a temperature from 10° C. to 90° C. to produce the 4-(5-bromo-6-methoxy-2-naphthyl)-4-hydroxybut-3-en-2-one of formula IV

IV

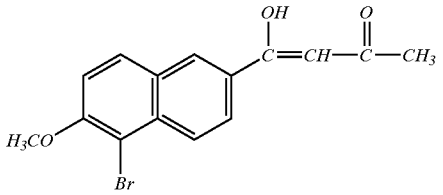

then acidifying the compound of formula IV at a pH value from 3 to 5 with an aqueous solution of an organic or inorganic acid;

b) catalytically hydrogenating one molar equivalent of the compound of formula IV with hydrogen at a pressure from 1 to 10 atmospheres, for a period of time from 2 to 24 hours, at a temperature from room temperature to 90° C., in presence of from 0.005 to 0.05 molar equivalents of a hydrogenation catalyst and from 0.30 to 0.99 molar equivalents of a base in a solvent selected from the group consisting of a polar solvent, a mixture of polar solvents and a mixture of polar and non-polar solvents;

c) filtering the product of step b) and concentrating the product under vacuum;

d) purifying the result of step c) either by crystallizing the compound of formula I from an alcohol containing from 1 to 6 carbon atoms; or by forming a crystalline bisulfite complex by reacting the result of step c) with sodium bisulfite in a polar solvent or a mixture of a polar solvent with water, and treating the resulting bisulfite complex with an aqueous solution of a hydroxide, carbonate or bicarbonate of an alkali metal to thereby recover the purified 4-(6-methoxy-2-naphthyl)butan-2-one of formula I.

38. The process of claim 37 wherein the alkaline alcoholate is selected from the group consisting of sodium or potassium alcoholates of alcohols having from 1 to 4 carbon atoms, the hydrogenation catalyst is 5% or 10% palladium on carbon, the base is selected from the group consisting of acetates and carbonates of sodium or potassium in an amount of from 0.90 to 0.98 molar equivalents; and hydrogeration conducted in a solvent selected from the group consisting of alcohols having from 1 to 6 carbon atoms, mixtures of alcohols having from 1 to 6 carbon atoms with water, and non-polar solvents.

39. The process of claim 37 wherein step a) in conducted in a solvent selected from the group consisting of toluene, acetonitrile, N,N-dimethylformamide and mixtures thereof.

40. A process for the synthesis of 4-(6-methoxy-2-naphthyl)butan-2-one of formula I

I

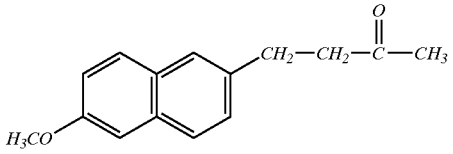

which comprises:

a) reacting one molar equivalent of 2-acetyl-5-bromo-6-methoxynaphthalene of formula II

IV

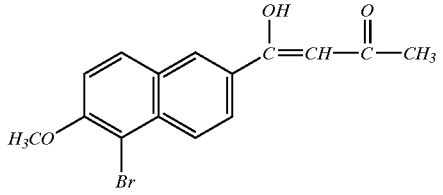

with an alkyl acetate of formula III

III

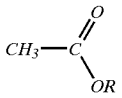

wherein R represents an alkyl group containing from 1 to 6 carbon atoms, in a solvent selected from the group consisting of the alkyl acetate of formula III, and mixtures of the alkyl acetate of formula III with toluene, acetonitrile or N,N-dimethylformamide; and in the presence of 1–3 molar equivalents of an alkaline alcoholate which is a sodium or potassium alcoholate of an alcohol containing from 1 to 4 carbon atoms, to form 4-(5-bromo-6-methoxy-2-naphthyl)-4-hydroxybut-3-en-2-one of formula IV:

IV

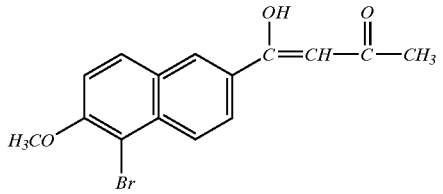

for from about 0.5 to about 6 hours and at a temperature of from about 10° C. to about 90° C.; then acidifying the compound of formula IV with an aqueous solution of an organic or inorganic acid at a pH of from 3 to 5;

b) reacting one molar equivalent of the compound of formula IV with hydrogen, in the presence of 0.005 to 0.05 molar equivalent of a 5% or 10% palladium on carbon hydrogenation catalyst and 0.30 to 0.99 molar equivalent of a base selected from the group consisting of an acetate or a carbonate of sodium or potassium; in a solvent comprising an alcohol having from 1 to 6 carbon atoms, mixtures of an alcohol having from 1 to 6 carbon atoms with water, or non-polar solvents; at a pressure of from 1–10 atmospheres, a temperature of from room temperature to 90° C. and for a period of time of 2–24 hours;

c) filtering the product of step b) to recover the compound of formula I and concentrating the compound of formula I under vacuum; and purifying the compound of formula I either by crystallizing the compound of formula I from an alcohol containing from 1 to 6 carbon atoms or forming a crystalline bisulfite complex by reacting the product of step b) with sodium bisulfite in a polar solvent or a mixture of a polar solvent with water, and treating the resulting bisulfite complex with an aqueous solution of a hydroxide, carbonate or bicarbonate of an alkali metal to thereby recover the purified 4-(6-methoxy-2-naphthyl)butan-2-one of formula I.

* * * * *